United States Patent [19]

Schopflin

[11] 4,012,497
[45] Mar. 15, 1977

[54] DRUG EXCIPIENT OF SILICONE RUBBER
[75] Inventor: Gisela Schopflin, Berlin, Germany
[73] Assignee: Schering Aktiengesellschaft, Berlin & Bergkamen, Germany
[22] Filed: Sept. 23, 1975
[21] Appl. No.: 616,001
[30] Foreign Application Priority Data
Sept. 24, 1974 Germany .......................... 2445971
[52] U.S. Cl. ................................. 424/22; 128/130; 128/260; 424/14; 424/15; 424/16; 424/19; 424/28
[51] Int. Cl.² ........................................ A61K 9/00
[58] Field of Search .......................... 128/260, 130; 424/14–22, 28

[56] References Cited
UNITED STATES PATENTS

| | | | |
|---|---|---|---|
| 3,279,996 | 10/1966 | Long et al. | 424/32 |
| 3,545,439 | 12/1970 | Duncan | 128/130 |
| 3,920,805 | 11/1975 | Roseman | 424/15 |

FOREIGN PATENTS OR APPLICATIONS

| | | |
|---|---|---|
| 2,158,226 | 5/1973 | Germany |

*Primary Examiner*—Shep K. Rose
*Attorney, Agent, or Firm*—Millen & White

[57] ABSTRACT

Nontoxic sustained release pharmaceutical compositions containing one or more nonionic, lipophilic drugs in a cured low temperature vulcanizable (LTV) silicone elastomer excipient are prepared substantially free of toxic vulcanizing agents or drug-reactive by-products in the elastomeric material by curing with a vulcanizable composition comprising
  a. a polydimethylsiloxane having vinyl groups on both ends;
  b. a copolymer consisting essentially of $SiO_2$ units, $(CH_3)_3SiO_{0.5}$ units, Vinyl$(CH_3)_2SiO_{0.5}$ units; and
  c. a cross-linking Si-H component, consisting essentially of $(CH_3)_3SiO_{0.5}$ units, $(CH_3)_2SiO$ units, and $CH_3HSiO$ units.

The resultant compositions are characterized by good physical properties and a constant rate of drug release in the body over long periods of time.

9 Claims, No Drawings

DRUG EXCIPIENT OF SILICONE RUBBER

CROSS-REFERENCE TO RELATED APPLICATIONS

This application is related to copending, commonly assigned U.S. Patent Application Ser. No. 444,886 filed Feb. 22, 1974 which in turn is a continuation-in-part of U.S. Patent Application Ser. No. 307,940 filed Nov. 20, 1972 and both now abandoned, and of U.S. Patent Application Ser. No. 530,385 filed Dec. 6, 1974, now abandoned the contents of which applications are incorporated by reference herein.

BACKGROUND OF THE INVENTION

This invention relates to organopolysiloxane molding composition drug excipients having a regular, uniform and prolonged drug dispensation rate, the use of such carriers for the production of medicinal agents and the medicinal agents prepared therefrom.

Organopolysiloxane elastomers in general are known to be suitable carrier materials for depot drug preparations providing long-term treatment in a living organism, since they are neither degraded nor resorbed by the organism and show a good tissue compatibility as compared to other synthetic polymers.

Nonionic, lipid-soluble medicaments enclosed in organosiloxane elastomers and in organosiloxane-resin-reinforced organopolysiloxane elastomers are released with a delay from the carrier material, e.g. as has been described by Kincl et al, Steroids 11(5) : 675–680 (1968); Dzuik and Cook, Endocrinology 78:208–211 (1966); Carrett and Chemburkar, J. Pharm. Sci. 57:1401–1409 (1968); and DOS (German Unexamined Laid-Open Application) 2,158,226.

The use of solid organopolysiloxane elastomers and organopolysiloxane elastomers reinforced with an organosiloxane resin as drug excipients with a controlled drug release of medicament is known and has been described, inter alia, in U.S. Pat. No. 3,279,996; British Pat. No. 998,794; DOS's 1,467,861; 1,900,196; 1,912,343; and 2,158,226.

The following organopolysiloxane elastomer raw materials are customary for the preparation of medication carriers:

1. Thermosetting organopolysiloxanes to be vulcanized with peroxide curing catalysts, e.g. benzoyl peroxide or di-p-chlorobenzoyl peroxide at temperatures of about 200° C. and requiring a heat aftertreatment, e.g. those described in U.S. Pat. Nos. 2,541,137; 2,723,966; 2,863,846; 2,890,188 and 3,002,951.

2. Hydroxyl-terminated organopolysiloxanes of the RTV (room temperature vulcanizing) type have been employed which harden to elastomers at room temperature after the addition of cross-linking agents in the presence of curing catalysts and under the atmospheric humidity. Typical curing catalysts are metallic salts of carboxylic acids, preferably tin salts, e.g. tin (II) octoate and tin (II)-2-ethylhexanoate.

3. Single-component silicone rubber compositions which are cured at room temperature under atmospheric humidity without any further additives are also known. These singlecomponent compositions contain primarily organopolysiloxanes with two terminal-positioned hydrolyzable acyloxy groups, e.g. acetoxy; the acyloxy groups are hydrolyzed under atmospheric humidity to form trifunctional siloxane units which cross-link the polymer into a cured elastomer. Such organopolysiloxanes are described, e.g., in U.S. Pat. Nos. 2,927,907 and 3,035,016 and in British Pat. Nos. 798,669 and 804,199.

These latter polysiloxane elastomers are obtained by thermosetting linear organopolysiloxanes and are utilized only in the preformed vulcanized condition to prepare drug excipients. Vulcanization of organopolysiloxane containing the drug is impossible, since almost all useful drugs are unstable either at the required high vulcanizing temperature and/or in the presence of peroxide catalysts.

4. Two-component dimethylpolysiloxane compositions, platinum-catalyzed at room temperature or under slightly elevated temperature and capable of addition cross-linking are also suitable as a carrier material for long-term delayed release depot drugs, e.g. see U.S. Pat. Application Ser. No. 444,886 filed Feb. 22, 1974 and corresponding DOS 2,158,226. In most cases, dimethylpolysiloxanes are used having one vinyl group on the chain end; the vinyl groups, however, need not be terminal-positioned. As the cross-linking agent, a methyl hydrogen polysiloxane is used having the general formula

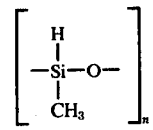

which can optionally also contain dimethylpolysiloxane groupings, but which contains at least 3 H atoms in the molecule as described in "Chemiker-Zeitung" (Chemist's News) 97(4):178–179 (1973).

According to DOS 2,158,226, LTV silicone rubber two-component compositions of the type disclosed in U.S. Pat. No. 2,823,218 consisting of (a) 85–95% by weight linear dimethylpolysiloxane containing maximally 0.5 molar percent methylvinylsiloxane units and having a molecular weight of 20,000–50,000, with (b) correspondingly 15–5% by weight of a dimethylpolysiloxane having an average molecular weight of 500–1,000, containing preferably 2 or 3 Si-H linkages per molecule, catalyzed with platinum or platinum compounds such as hexachloroplatinic acid, are utilized as medication carriers for depot drug preparations for the long-term treatment in a living organism.

Similarly suitable as a carrier material for the preparation of long-term depot drug compositions, according to DOS 2,158,226, are platinum-catalyzed dimethylpolysiloxane two-component compositions which are capable of addition cross-linking and consist of 85–89% by weight of the aforementioned dimethylpolysiloxane containing maximally 0.5 molar percent of methylvinylsiloxane units, 5–10% by weight of the aforementioned dimethylpolysiloxane with Si-H bonds, and 5–10% of a dimethylpolysiloxan resin having no more than 1.2 molar percent of methylvinylsiloxane units as an auxiliary cross-linking agent, catalyzed with a platinum compound.

The use of such dimethylpolysiloxane two-component compositions capable of additional cross-linking as medication carriers for depot drug forms often fails due to the fact that these compositions can be converted into usable vulcanizates only in admixture with medicaments which are chemically almost saturated substances. Olefinically and especially multiolefinically or acetylenically unsaturated compounds, e.g. 3-methoxy-19-nor-17α-pregna-1,3,5(10)-trien-20-yn-17-ol (mestranol) and ethynylestradiol, in admixture with these LTV silicone rubber two-component compositions prevent vulcanization of the silicone base.

OBJECTS OF THE INVENTION

Accordingly, it is a general object of this invention to provide new and improved elastomer drug excipients.

Another object of this invention is to provide sustained release pharmaceutical compositions having an improved excipient as the matrix for a pharmaceutically active ingredient and a process for their preparation.

A further object of this invention is to provide drug implants which exhibit a uniform rate of drug release over a long period of time.

An additional object of this invention is to provide a process for maintaining a uniform drug concentration in a living animal over an extended period of time with a single dosage.

A more particular object of this invention is to provide improved excipients for chemically unsaturated, e.g. olefinically and especially multiolefinically unsaturated medicaments, particularly steriods, prostaglandins and the like.

Upon further study of the specification and appended claims, further objects and advantages of this invention will become apparent to those skilled in the art.

SUMMARY OF THE INVENTION

The above and other objects are attained in one aspect of this invention by providing a vulcanizable composition capable of being catalytically cured with a platinum metal-based vulcanization catalyst in the presence of a pharmaceutically active amount of a nonionic, lipophilic drug to form a nontoxic elastomeric sustained release pharmaceutical composition, said vulcanizable composition consisting essentially of:

a. a polydimethylsiloxane having vinyl groups on both ends;

b. a copolymer consisting essentially of $SiO_2$ units, $(CH_3)_3SiO_{0.5}$ units, Vinyl$(CH_3)_2SiO_{0.5}$ units; and c. a cross-linking Si-H component, consisting essentially of $(CH_3)_3SiO_{0.5}$ units, $(CH_3)_2SiO$ units, and $CH_3HSiO$ units.

DETAILED DISCUSSION

It has now been found that it is surprisingly possible to produce medication carriers for long-term use with lipophilic, nonionic active medicinal agents, independently of the degree of unsaturation of the substances, by using as carrier material an LTV organopolysiloxane two-component molding composition which contains a silicone copolymer. These platinum-catalyzed silicone rubber two-component compositions of the LTV type are known per se, e.g. see DAS (German Published Applications) 1,171,641 and 1,900,969; DOS 1,940,124; U.S. Pat. Nos. 2,970,150; 2,823,218; 3,159,601; 3,159,662; 3,220,972; and 3,271,362.

The LTV organopolysiloxane two-component molding compositions, conventionally curable by the addition of a platinum catalyst, which are useful in accordance with the present invention, are characterized by containing vinyl groups and organopolysiloxane mixtures containing silicon-bound hydrogen atoms and comprise:

I. 20–100 parts by weight of vinyl terminated linear organopolysiloxane having a viscosity of 500–200,000 centistokes (at 25° C.) of the general formula:

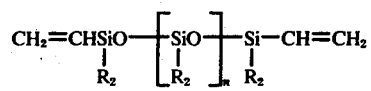

wherein $R_2$ is alkyl of 1–8 carbon atoms, preferably methyl, and/or phenyl residue and n is an integer of 200–1600 inclusive, preferably 500–1000;

II. 0–50 parts by weight of an organopolysiloxane copolymer consisting essentially of:

a. $R'_3 SiO_{0.5}$ units, b. $R'_2ViSiO_{0.5}$ units, and c. $SiO_2$ units, wherein Vi is a vinyl group, $R'_2$ and $R'_3$ are each a saturated, monovalent, organic residue which does not contain any carbon-carbon olefinically or acetylenically unsaturated groups, e.g. an aliphatic group, preferably alkyl of 1–8 carbon atoms and especially methyl, and wherein at least 50% of R' is methyl; the ratio of $a+b/c$ is 0.4–1.5, preferably 0.6–1.0; and the ratio of $b/c$ is 0.02–0.5, preferably 0.05–0.15;

III. 5–15 parts by weight of an organohydrogen polysiloxane of the general formula

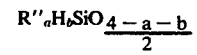

wherein

R" is a monovalent residue as defined for $R'_2$ and $R'_3$ which has no unsaturated groups; a and b are each positive numbers of 0.1–2.5, preferably 0.9–1.4; the ratio of $a:b$ has a value of 0.5–10, preferably 1.0–5; the sum of $a + b$ is equal to 1 to 2.5; and wherein at least three hydrogen atoms linked to different Si atoms are present per molecule, which component contains 50–500 molar percent, based on the unsaturated groups contained in components (I) and (II), of vinyl groups attached to Si-H, and IV. a catalytic amount of platinum or a platinum compound curing catalyst such as hexachloroplatanic acid.

Components I, II and IV form the curable component of the LTV organopolysiloxane two-component molding composition, while component III constitutes the second component having a cross-linking effect. Component I and/or the mixture of components I, II and IV or I, II, II and IV can optionally contain cure retardants to inhibit curing at room temperature, e.g. copper (II) ions in an amount of 2.61–75 parts by weight of metallic ions per part by weight of platinum.

Although vulcanization of the organopolysiloxane molding compositions in the presence of the noble metal catalyst can take place at room or body temperature, vulcanization at a slightly elevated temperature, e.g. of 40°–120° C., is especially advantageous. The vulcanizing time of the catalyzed mixture is generally 1 to 6 hours at 60°–120° C. It is to be noted that no by-products are formed during the vulcanization. For this reason, subsequent heat treatment of the cured product is superfluous.

The platinum-containing component IV of the molding composition can be used in one of the conventional forms known for catalyzing the reaction between silicon-linked hydrogen residues and silicon-linked vinyl residues. Such suitable forms include but are not limited to metallic platinum; platinum on support materials such as silica gel and/or pulverized carbon; or platinum salts, e.g. hexachloroplatinic acid, platinum carbonyl dichloride $PtCOCl_2$ or platinum dicarbonyl dichloride $Pt(CO)_2Cl_2$. All of these platinum compounds are usable as catalysts for the molding compositions of the present invention.

Platinum compound catalysts utilized in the solid form cause the cross-linking reaction to proceed slowly but with little control thereover, so that the cross-linking reaction can be interrupted more readily than with the use of comparable catalysts in solution. Hexachloroplatinic acid when used as the catalyst is preferably dissolved in isopropanol, and $PtCOCl_2$ and $Pt(CO)_2Cl_2$ are preferably used as a solution in a vinyl-group-containing diorganopolysiloxane containing 10–15 molar percent vinyl groups. At least 0.1 part by weight of platinum must be used per 1 million parts by weight of I and II. Since impurities in the molding composition can poison such small quantities of catalyst, 10–40 ppm of platinum is preferably employed. Larger amounts of platinum do not impair the reaction but are uneconomical.

The molding compositions of the present invention are inactive with respect to nonionic lipophilic drugs; nontoxic; physiologically compatible, and cannot be absorbed by the living organism. They are substantially free of peroxide, acetic acid, metal salts of carboxylic acids which are toxic to a living organism and other toxic curing by-products which have severely limited the use of prior art silicone excipients.

The drug excipients of the present invention are suitable as vehicles for one or more nonionic, lipophilic drugs. By the term nonionic as used herein is meant those drugs which, in the condition in which they are to be administered or bound in the excipient matrix of the present invention, exhibit dissociation constants of less than about $10^{-7}$.

By the term lipophilic as used herein is meant those drugs which, in the condition in which they are to be bound in the excipient matrix of the present invention, are soluble or miscible in conventional fat solvents, e.g. ether, chloroform, benzene, etc. The drugs can be bound singly or in admixture and in pure form or with conventional additives. The additives are, e.g. lactose, magnesium stearate, highly dispersed barium sulfate with a particle size smaller than 4 μm and silicon oil with a molecular weight of 300–20,000.

The medications produced with the carrier material used according to this invention provide a reliable source of medicines to be administered over long periods of time which can be readily introduced, easily retained and removed without difficulties, exhibiting an uninterruptedly useful effect on humans and animals. With the aid of this source, it is possible to continuously administer medicinal agents during precisely defined medication periods.

Suitable drugs with which, in a novel, effective manner, undesired conditions in or at the human or animal organism are to be treated or controlled and which exhibit these properties include but are not limited to hormones, e.g. cyproterone acetate, progesterone, estradiol, testosterone, insulin, triiodthyronin and cortisone, prostaglandins, e.g. prostaglandine $E_1$, prostaglandine $E_2$, prostaglandine $A_1$ and prostaglandine $F_2$ ; vitamins, e.g. vitamin A, vitamin $D_2$, vitamin $D_3$, vitamin E, vitamin $K_1$, vitamin $K_2$ and derivatives of vitamin $B_1$, e.g. thiamine tetrahydrofurfuryl disulfide or thiamine propyldisulfide; antibiotics, e.g. erythromycin and tetracycline; contraceptives, e.g. chlormadinone, chlormadinone acetate, megestrol acetate, d-norgestrel, medroxyprogesterone acetate; and spermicides, e.g. p-diisobutylphenoxypolyethoxyethanol. The drugs are employed in at least the pharmaceutically active amounts known in the art, preferably in a 1,000 fold excess.

The medication carriers of this invention are suitable, in particular, for the production of depot drug preparations with nonionic, lipid-soluble active medicinal agents containing olefinic or acetylenic unsaturated bonds in the molecule, due to the special structure of these carriers. Illustrative active medicinal agents of this type include but are not limited to 3-methoxy-19-nor-17α-pregna-1,3,5(10)-trien-20-yn-17-ol (mestranol) ethynylestradiol, 3-cyclopentoxy-17α-ethynyl-1,3,5(10)-estratrien-17βol, 17α-ethynyl-17β-hydroxy-4-androsten-3-one (ethisterone), 17β-hydroxy-6α-methyl-17α-(1-propynyl)-4-androsten-3-one (dimethisterone), 17β-hydroxy-17α-ethynyl-19-nor-4-androsten-3-one (norethisterone), 17β-acetoxy-17α-ethynyl-19-nor-4-androsten-3-one (norethisterone acetate), 17β-hydroxy-17α-ethynyl-19-nor-5(10)-androsten-3-one (norethynodrel), 17β-hydroxy-17α-vinyl-5(10)-estren-3-one (vinylestrenolone), 3β,17β-diacetoxy-17α-ethynyl-4-estrene (ethynodiol acetate), 17α-ethynyl-19-nor-4-androsten-17β-ol (lynestrenol), 3-cyclopentoxy-17β-acetoxy-17α-ethynyl-3,5-estradiene (quingestanol acetate), DL-17β-hydroxy-13β-ethynyl-17α-ethynyl-4-gonen-3-one (DL-norgestrel), D-norgestrel, 17α-acetoxy-16-methylene-4,6-pregnatriene-3,20-dione, 17β-hydroxy-17α-ethynyl-4,9,11-estratrien-3-one (norgestrienone) and 17β-heptanoyloxy-17α-ethynyl-4-estren-3-one (norethisterone enanthate).

The medication carriers of the present invention have the advantage that the incorporated medicinal agent is released with uniform delay in an exactly controllable degree even in the minute dose. Thereby, a uniform and constant level of active agent is maintained in the living organism during a predetermined time span, e.g. of many months, during which physiological effects are desirable. The medication carriers of this invention generally contain the active ingredient in an amount of 10–60%, preferably 30–55% by weight, based on the total weight of the preparation.

Another important feature of the medication carriers of this invention is that their shape can be arbitrarily selected since vulcanization of the organopolysiloxanes used in accordance with this invention is equally possible in closed and open systems and neither the degree of curing nor the curing rate are impaired by the effect of atmospheric humidity. Thus, the desired form can be determined only by the type and amount of the medicinal agent to be administered, the desired drug release rate from the carrier and the location of administration.

The desired medicinal agents are produced from the carrier material by mixing the components with the active drug and then vulcanizing the admixture at an elevated temperature, preferably at 40°–120° C. The medicinal agents are then constructed entirely or partially according to the matrix principle. However, it is also possible to make the medicinal agents of a core containing the drug and of an outer silicone elastomer shell casing with a low drug content and having any desired layer thickness; conversely, these agents can consist of a core element low in drug content surrounded by an elastomer shell layer containing the active drug. Such a shell of low drug content over a core enriched with the active drug with a predominantly suspended active agent is conveniently obtained, for example, by short-term extraction of medicinal agents built up on the matrix principle with a suitable solvent, e.g. ethanol: water = 1:1. The variation in concentration of effective agent between the high and low concentration layers can be one hundred fold or higher, but is generally 1 to 60 fold, preferably 10 to 50 fold. The medicinal agents can also be produced in the form of prosthetic devices for the body from which the effective agent is released with a delay, and are especially useful as IUD's, e.g. of the type described in U.S. Patent Application Ser. No. 530,385 filed December 6, 1974. If necessary, it is also possible to inject catalyzed elastomer raw material and active drug mixtures in vitro and complete vulcanization at the predetermined location where the drug is to be effective.

For special applications, it is useful to provide the medication carrier with a retrieval thread of a suitable material such as surgical silk and to introduce the carrier into a suitable applicator.

Also, the drug carrier can comprise, if desired, a core enriched in the active drug made up of the active agent or agents and auxiliary substances which are not markedly soluble in the silicone elastomer or which bring about the release of the effective drugs from the drug carriers to the desired extent, and an LTV silicone elastomer casing disposed thereon which is low in drug content or likewise enriched in drug content.

The medicinal agents of this invention can be implanted at the organ to be treated, as well as at other locations in the body where a drug-evoked effect is desirable, or they can be introduced for this purpose into body cavities. For improved X-ray localization in the body, the active agent carrier can contain a radiopaque amount of barium sulfate.

By means of the carriers of this invention, many active drug agents can be utilized successfully which could not be applied by means of the heretofore known and customary carrier materials in suitable drug preparations, e.g. for intrauterine or intravaginal administration of medicinally active agents.

The medication carrier of this invention can also be used for introducing a basic dosage of the active agent while a temporarily required higher dosage can be conventionally administered by oral or parenteral application.

The active agents are preferably contained in the carrier material in suspended form, since solids are normally more chemically stable than solutions and thus can be advantageously transported to the site of application. To produce a suspension, the active agents are preferably processed in the dry, pulverized form so that they are homogeneously dispersed throughout the carrier material predominantly in the practice size optimal for the intended purpose, or they can be more or less compressed and surrounded by the elastomer in the carrier material. The more water-soluble the active medicinal agent, the larger are the selected particles. The particle size suitably ranges from about 2 to about 500 $\mu$, preferably 4–400 $\mu$.

The drug excipients according to this invention can be conventionally sterilized in saturated, pressurized steam at 120° C. without incurring any undesired changes.

The medicines made of LTV-silicone elastomer according to this invention have a Shore A hardness (DIN 53 505) of 45–70. Accordingly, they do not crumble upon mechanical stress and are less susceptible to damage by handling with metallic instruments during their introduction into the organism in comparison with RTV-elastomer excipients of the prior art, to which must often be added fillers with their disadvantageous drug absorption properties in order to improve the mechanical characteristics of the medicine.

Without further elaboration, it is believed that one skilled in the art can, using the preceding description, utilize the present invention to its fullest extent. The following preferred specific embodiments are, therefore, to be construed as merely illustrative, and not limitative of the remainder of the disclosure in any way whatsoever.

In the following Examples, the temperatures are set forth in degrees Celsius; unless otherwise indicated, all parts and percentages are by weight. The terms "curing", "vulcanizing"; "cross-linking", etc., are used interchangeably herein to refer to process by which the plastic organopolysiloxane is converted to a relatively elastic rigid product by the formation of chemical bridges between the polysiloxane chains.

EXAMPLE 1

5.5 g. of micronized 17$\beta$-acetoxy-17$\alpha$-ethynyl-4-estren-3-one (norethisterone acetate) is mixed with 4.5 g. of an organopolysiloxane molding composition, consisting of 75 parts by weight of a polydimethylsiloxane carrying vinyl terminal groups on both sides and having a viscosity of 50,000 cSt. at 25° C.; 25 parts by weight of a copolymer composed of: 40 mol-% $SiO_2$ units, 45 mol-% $(CH_3)_3SiO_{0.5}$ units and 15 mol-% $Vi(CH_3)_2SiO_{0.5}$ units; 8 parts by weight of a Si-H component consisting of: 16.6 mol-% $(CH_3)_3SiO_{0.5}$ units, 33.4 mol-% $(CH_3)_2SiO$ units, 50 mol-% $CH_3HSiO$ units; and 10 p.p.m. of platinum, based on the total mixture, in the form of a 2% solution of $H_2PtCl_6$ in isopropanol (= molding composition A). The norethisterone acetate is triturated without air bubbles in the organopolysiloxane molding composition and the composition is molded into cylinders with hemispheres attached to the ends, having a total length of 6 mm., a cylinder diameter of 5 mm., and a radius of curvature of the hemisphere of 2.8 mm. The molded articles are vulcanized by 2 hours of heating to 110° C. Medication carriers are obtained constructed according to the matrix principle, containing norethisterone acetate in a predominantly microcrystalline form. After sterilizing in tensioned steam during 1 hour at 120° C., the articles have a Shore A hardness of 55–56 and are intended for implantation.

EXAMPLE 2

60.0 g. of micronized D-13-ethynyl-17$\alpha$-ethynyl-17$\beta$-hydroxy-4-gonen-3-one (D-norgestrel) is processed with 40.0 g. of the organopolysiloxane molding composition A described in greater detail in Example 1 into a homogeneous suspension free of air bubbles. The suspension is shaped into cylinders having a length of 20 mm. with a diameter of 2.5 mm., and the cylinders are vulcanized by heating for 2 hours to 110° C. The molded articles are intended for implantation.

EXAMPLE 3

54.0 g. of micronized ethynylestradiol is worked into a homogeneous suspension with 5.0 g. of barium sulfate and 41.0 g. of an organopolysiloxane molding composition consisting of 75 parts by weight of a polydimethylsiloxane carrying terminal vinyl groups on both ends and having a viscosity of 1,000 cSt. at 25° C.; 25 parts by weight of a copolymer composed of: 40 mol-% $SiO_2$ units, 45 mol-% $(CH_3)_3SiO_{0.5}$ units, 15 mol-% $Vi(CH_3)_2SiO_{0.5}$ units; 8 parts by weight of a Si-H component consisting of 16.6 mol-% $(CH_3)_3SiO_{0.5}$ units, 33.4 mol-% $(CH_3)_2SiO$ units, 50.0 mol-% $CH_3HSiO$ units; and 10 p.p.m. of platinum, based on the total mixture, in the form of a 2% solution of $H_2PtCl_6$ in isopropanol (= molding composition B). The suspension is vented under vacuum and then shaped into cylinders having a length of 20 mm. with a diameter of 1.5 mm. and vulcanized by 2 hours of heating to 110° C. The shaped articles are intended for implantation.

EXAMPLE 4

58.0 g. of estradiol is triturated with 42.0 g. of an organopolysiloxane molding composition consisting of 85 parts by weight of a polydimethylsiloxane terminated on both sides with vinyl end groups and having a viscosity of 1,000 cSt. at 25° C.; 15 parts by weight of a copolymer composed of: 40 mol-% $SiO_2$ units, 45 mol-% $(CH_3)_3SiO_{0.5}$ units, 15 mol-% $Vi(CH_3)_2SiO_{0.5}$ units; 4.5 parts by weight of a Si-H component consisting of: 38 mol-% $SiO_2$ units, 29 mol-% $(CH_3)_3SiO_{0.5}$ units, 33 mol-% $(CH_3)_2HSiO_{0.5}$ units; and 10 p.p.m. platinum, based on the total mixture, in the form of a 2% solution of $H_2PtCl_6$ in isopropanol (= molding composition C). The triturated product is processed, as described in Example 3, to cylindrical implants of a length of 20 mm. and a diameter of 1.5 mm.

EXAMPLE 5

Cylindrical implants are produced, as set forth in Example 1, from 20.0 g. of micronized D-13-ethynyl-17α-ethynyl-17β-hydroxy-4-gonen-3-one (D-norgestrel) with 20.0 g. of highly disperse silicon dioxide and 60.0 g. of an organopolysiloxane molding composition, consisting of 75 parts by weight of a polydimethylsiloxane, terminated on both sides by vinyl end groups and having a viscosity of 1,000 cSt. at 25° C.; 25 parts by weight of a copolymer of the composition: 40 mol-% $SiO_2$ units, 45 mol-% $(CH_3)_2SiO_{0.5}$ units, 15 mol-% $Vi(CH_3)_2SiO_{0.5}$ units; 8 parts by weight of a Si-H component consisting of: 16.6 mol-% $(CH_3)_3SiO_{0.5}$ units, 33.4 mol-% $(CH_3)_2SiO$ units, 50.0 mol-% $CH_3HSiO$ units; and 30 p.p.m. of platinum, based on the total mixture, in the form of a 1% solution of $Pt(CO)_2Cl_2$ in an open-chain dimethylpolysiloxane containing vinyl groups in the amount of 12 mol-%, and 5 parts by weight, based on the parts by weight of platinum, of Cu(II) ions (= molding composition D).

EXAMPLE 6

62.0 g. of 17α-ethynyl-19-nor-testosterone acetate (norethisterone acetate) is made into a suspension with 38.0 g. of an organopolysiloxane molding composition composed as follows: 75 parts by weight of a polydimethylsiloxane carrying vinyl ends groups on both sides and having a viscosity of 50,000 cSt. at 25° C.; 25 parts by weight of a copolymer of the composition: 40 mol-% $SiO_2$ units, 45 mol-% $(CH_3)_3SiO_{0.5}$ units, 15 mol-% $Vi(CH_3)_2SiO_{0.5}$ units; 8 parts by weight of a Si-H component consisting of: 16.6 mol-% $(CH_3)_3SiO_{0.5}$ units, 33.4 mol-% $(CH_3)_2SiO$ units, 50 mol-% $CH_3HSiO$ units; and 35 p.p.m. of platinum, based on the total mixture, in the form of a 1.5% solution of $Pt(CO)_2Cl_2$, dissolved in a vinyl-group-containing dimethylpolysiloxane containing 15 mol-% vinyl groups (= molding composition E), and processed as indicated in Example 2 into cylindrical implants.

EXAMPLE 7

20.0 g. of micronized D-norgestrel is suspended under aseptic conditions in 54.0 g. of a polydimethylsiloxane carrying vinyl end groups on both sides and having a viscosity of 50,000 cSt. at 25° C.; 18.0 g. of a copolymer composed of: 40 mol-% $SiO_2$ units, 45 mol-% $(CH_3)_3SiO_{0.5}$ units, 15 mol-% $Vi(CH_3)_2SiO_{0.5}$ units; and 10 p.p.m. of platinum (based on 54.0 g. of polydimethylsiloxane carrying vinyl end groups on both sides) in the form of a 1% solution of $Pt(CO)_2Cl_2$ in a vinyl-group-containing dimethylpolysiloxane with 10 mol-% vinyl groups. Respectively 0.9 ml. of this suspension and 0.1 ml. of sterile-filtered Si-H component consisting of: 16.6 mol-% $(CH_3)_3SiO_{0.5}$ units, 33.4 mol-% $(CH_3)_2SiO$ units, and 50 mol-% $CH_3HSiO$ units is filled, after two hours of exposure to vacuum at 150 mm. Hg, into two-chamber injection syringes. The two thus-dispensed components of the preparation filled into these syringes can be mixed together shortly before the intended injection; the catalyzed suspension containing the active agent is vulcanized within the organism at the predetermined location.

EXAMPLE 8

25.0 g. of micronized progesterone is processed into a suspension with 75.0 g. of the organopolysiloxane molding composition E described in Example 6. From this suspension, vaginal caps are produced by shaping and subsequent vulcanization for 2 hours at 100° C., these caps having a diameter of 3 cm., a layer thickness of 0.3 cm., and a radius of curvature of 1.5 cm., with a height of 2 cm. and a central bore having a diameter of 8 mm.

EXAMPLE 9

18.0 g. of micronized ethynylestradiol is suspended in 82.0 g. of an organopolysiloxane molding composition consisting of: 75 parts by weight of a polydimethylsiloxane carrying vinyl end groups on both sides and having a viscosity of 50,000 cSt. at 25° C.; 25 parts by weight of a copolymer composed of: 40 mol-% $SiO_2$ units, 45 mol-% $(CH_3)_3SiO_{0.5}$ units, 15 mol-% $Vi(CH_3)_2SiO_{0.5}$ units; 8 parts by weight of a Si-H component consisting of: 16.6 mol-% $(CH_3)_3SiO_{0.5}$ units, 33.4 mol-% $(CH_3)_2SiO$ units, 50 mol-% $CH_3HSiO$ units; and 25 p.p.m. of platinum, based on the total mixture, in the form of a 2% solution of $Pt(CO)_2Cl_2$ in a dimethylpolysiloxane containing 10 mol-% vinyl groups (= molding composition F). The suspension is poured on the side of a dental prosthesis facing the palate in a layer thickness of 1.5 mm. and in an amount of 300 mg. after the actual prosthesis material has been degreased; the layer is vulcanized by three hours of heating to 80° C.

EXAMPLE 10

30.0 g. of norethisterone acetate is triturated with 70.0 g. of the organopolysiloxane molding composition F as described in Example 9. The suspension is poured into molds representing cylinders with hemispheres attached at the ends and having, with a radius of curvature of the hemisphere of 2.8 mm. and a cylinder diameter of 6 mm., a total length of 15 mm. These molds are also provided with an inserted stainless steel ($V_2A$) thread having a diameter of 0.4 mm. and projecting from the molds by about 3 cm. at the cylinder ends. By heating the suspension for 3 hours to 120° C., medication carriers are obtained which are fixed in the oral cavity by means of the attached stainless steel wires and by means of the fixed braces customary in jaw orthopedics, which are used for jaw correction.

EXAMPLE 11

45.0 g. of megestrol acetate is mixed with 55.0 g. of the organopolysiloxane molding composition F as described in Example 9. The triturated product is pressed into cylindrical molds having a diameter of 2.5 mm. and a length of 4 mm. with surgical thread inserted therein having a thickness of the grade 2 EP I and forming outside of the mold a loop of a length of 8 cm. The product is vulcanized by heating for 3 hours to 90° C. The vulcanizates are centered by means of the inserted threads in cylindrical molds having a diameter of 3.5 mm. and a length of 6 mm. The cavity remaining in the molds is filled out with organopolysiloxane molding composition E as described in Example 6. By heating for 90 minutes to 100° C., the covering, free of medicinal agent, is vulcanized onto the megestrol-acetate-containing silicone elastomer carrier. The molded articles with retrieval strings are intended for intrauterine application.

EXAMPLE 12

30.0 g. of norethisterone acetate is suspended with 24.0 g. of highly disperse silicone dioxide in 46.0 g. of the organopolysiloxane molding composition F as disclosed in Example 9. From the suspension, thread material having a diameter of 0.5 mm. is produced by molding and 2 hours of vulcanizing at 110° C. This thread material is worked, together with cotton threads, into a fabric strip having a width of 2 cm. and a length of 2.5 cm., with linen binding, intended for intravaginal application. The fabric has, in the warp, a thread density of 12 threads per centimeter, wherein each third thread is a silicone elastomer thread containing medicinal agent, and cotton thread of 17 g./1000 m. is incorporated by weaving. In the weft, the fabric has a thread density of 8 threads per centimeter and contains cotton threads of 14 g./1000 m. The fabric releasing norethisterone acetate is provided in the warp additionally with a cotton string having a thickness of 2 mm., provided as the retrieval thread.

EXAMPLE 13

Thread material based on the organopolysiloxane molding composition F is produced, as described in Examples 9 and 12, respectively, with the use of norethisterone acetate as the active medicinal agent. The thread material is worked into a fabric with linen binding of a width of 2 cm. and a length of 2 cm., containing in the warp 6 threads and in the weft 4 threads per centimeter. On both sides of this fabric, a layer of cellulose wadding, 0.1 cm. thick, is applied. The drug-containing fabric and the cellulose layers are joined by a cotton thread having a diameter of 1.5 mm. woven into the fabric centrally in the longitudinal direction and simultaneously fashioned as a retrieval string. The entire arrangement is rolled up into a vaginal tampon having a length of 2 cm. and a diameter of 1.2 cm.

EXAMPLE 14

A suspension of 50 parts by weight of micronized mestranol in 50 parts by weight of the organopolysiloxane molding composition E as described in Example 6 is rolled out to a layer thickness of 1 mm. and vulcanized by 3 hours of heating to 90° C. From this sheet, strips having the dimensions of 15 × 30 mm. are cut and affixed centrally to polyamide films having the dimensions of 25 × 45 mm., coated on one side with a polyacrylate adhesive. The uncovered adhesive film and the opposite side of the film are provided with cover strips which are easily removable and overlap in the middle.

The polyacrylic adhesive composition used in this connection is preferably a copolymer of acrylic acid and isooctyl acrylate in a molar ratio of about 6 : 94. From plasters of this type, the mestranol becomes effective systemically during long-term usage after absorption through the skin.

EXAMPLE 15

45.0 g. of mirconized 17α-ethynyl-19-nortestosterone enanthate is mixed homogeneously with 8.0 g. of highly disperse silicon dioxide, 5.0 g. of barium sulfate, and 42.0 g. of the organopolysiloxane molding composition A described in Example 1. The mixture is introduced into molds representing several spheres interconnected by round rods and having a Y-shaped contour. The molded articles are vulcanized by six hours of heating to 60° C., thus obtaining medication carriers for intrauterine application which, with a total length of 3.6 cm., have the following structure: Emanating from a central sphere having a diameter of 2.8 mm., three round rods of varying length ending in spheres, are arranged, these rods having a diameter of 1.4 mm. Two round rods terminate, with a length of 0.8 and 1.2 cm., respectively, in spheres having a diameter of 1.5 and 4.8 mm., respectively, and are arranged at an obtuse angle with regard to the third round rod. The third round rod is continued in the three round rod composite of four spheres having a diameter of 2.8 mm. into a bean-shaped end piece having a length of 4.5 mm. with a central bore of 1 mm. diameter. Into this eye, shaped as a bean-like end piece, is knotted 9 cm. of polyester thread having the thread thickness of 2 EP I (European Pharmacopoeia I) as an indicator and retrieval thread for the medication to be utilized by intrauterine application.

EXAMPLE 16

Medication carriers with 45 parts by weight of D-norgestrel of the form indicated in Example 15 are produced from molding composition A. The end spheres of a diameter of 1.5 and 4.8 mm., respectively, and the 4 stem spheres having a diameter of 2.8 mm. are coated with a layer, 20 μ thick, of a conductive cooper varnish containing 60 parts by weight of micronized electrolyte copper in a polyvinylidene resin solution. On this layer of conductive copper varnish is applied about 150 μ of copper by galvanic deposition.

Thus, these molded articles are coated partially with copper and contain D-norgestrel as the active agent. They are intended for intrauterine administration. Prior to application, the articles are provided with an indicator and retrieval thread of nylon, wherein the indicator thread is knotted into the bean-shaped eye of the medication carrier.

EXAMPLE 17

55 parts by weight of D-norgestrel-containing medication carrier having a Y-like contour is produced on the basis of the organopolysiloxane molding composition A in the dimensions set forth in Example 15. The medication carriers are provided, additionally to the indicator and retrieval thread, as indicated in Example 16, with a drug-containing thread containing 60 parts by weight of ethynylestradiol. This thread is produced on the basis of the organopolysiloxane molding composition E as described in Example 6. The active agent suspension in the molding composition is vulcanized by heating for 2 hours to 110° C. The thread has a diameter of 0.5 mm. and a length of 9 cm. and is knotted into the bean-shaped end piece of the medication carrier so that the article terminates in two thread ends having a length of about 4 cm. This form of medicine is intended for intrauterine application. The thread-like extension of the arrangement remains in the cervical canal after the medication carrier has been administered. The thread is sterilized together with the contraceptive in pressurized steam for a period of 30 minutes and then packaged under aseptic conditions.

EXAMPLE 18

35 parts by weight of estradiol is mixed homogeneously with 25 parts by weight of highly disperse silicon dioxide and 40 parts by weight of organopolysiloxane molding composition E as described in Example 6. From the suspension, rings are molded having an outer diameter of 6 cm. and an inner diameter of 4.2 cm. The thus-shaped suspension is vulcanized by heating for 2 hours to 110° C., thus obtaining medication carriers for intravaginal application.

EXAMPLE 19

15 parts by weight of norethisterone acetate is processed into a suspension with 31 parts by weight of highly disperse silicon dioxide and 54 parts by weight of organopolysiloxane molding composition E as described in Example 6. This suspension is molded into rings having the dimensions of those in Example 18 and being vulcanized by 2 hours of heating to 120° C. The ring-shaped medication carriers are meant for intravaginal administration.

EXAMPLE 20

A mixture of 10.0 g. of micronized D-norgestrel with 14.8 g. of lactose and 0.2 g. of magnesium stearate is compressed on a tabletting press in a conventional manner to biconvex tablets weighing 25 mg. and having a diameter of 3 mm. and a radius of curvature of 3 mm. The pressed articles are filled into metallic molds, preheated to 100° C. and having a diameter of 4 mm. and a radius of curvature of 4 mm., together with the D-norgestrel suspension in the organopolysiloxane molding composition D which contains highly disperse silicon dioxide, as described in Example 5. By the rapid initial vulcanization of the organopolysiloxane molding composition, the pressed article is well centered in the mold. The suspension is vulcanized by 2 hours of heating in the molds at 100° C. The shaped articles, containing D-norgestrel, are meant for implantation.

EXAMPLE 21

Analogously to Example 6, medication carriers containing norethisterone acetate are produced. The vulcanizates are extracted successively for 90 minutes with 96% strength ethanol, then another 30 minutes with 96% strength ethanol, for 60 minutes with 70% strength ethanol, and for 30 minutes with 50% strength ethanol at room temperature. After removing, by drying, the dilute ethanol still adhering to the vulcanizates, the medication carriers are sterilized under pressurized steam for 30 minutes, thus obtaining medication carriers having a casing of low norethisterone acetate content on a core enriched in norethisterone acetate, intended for implantation.

EXAMPLE 22

Medication carriers having a Y-like contour, intended for intrauterine use and containing D-norgestrel in a homogeneous suspension in the organopolysiloxane molding composition A, are produced as set forth in Example 16 and coated on the end and stem spheres with copper. Additionally, these medication carriers are galvanically coated with 50 $\mu$ of silver on copper on the end sphere having a diameter of 4.8 mm., on the stem sphere following the bean-shaped end pieces, and on the penultimate sphere having a diameter of 2.8 mm.

The preceding examples can be repeated with similar success by substituting the generically and specifically described reactants and/or operating conditions of this invention for those used in the preceding examples.

From the foregoing description, one skilled in the art can easily ascertain the essential characteristics of this invention, and without departing from the spirit and scope thereof, can make various changes and modifications of the invention to adapt it to various usages and conditions.

What is claimed is:

1. A non-toxic sustained release pharmaceutical composition in the form of a shaped object having a Shore A hardness of 45–70, consisting essentially of a safe and pharmaceutically active amount of a nonionic lipophilic drug having a dissociation constant of less than $10^{-7}$ and which is olefinically or acetylenically unsaturated and soluble in ether, chloroform or benzene, said drug being dissolved or uniformly suspended in a non-toxic vulcanized LTV linear dimethylpolysiloxane elastomer and said composition being prepared by reacting, at an elevated temperature and in contact with a catalytic amount of a platinum-based vulcanization catalyst capable of catalyzing the reaction between silicon-linked hydrogen residues and silicon-linked vinyl residues a mixture of said drug and a vulcanizable composition consisting essentially of:
  a. a polydimethylsiloxane having vinyl groups on both ends;
  b. a copolymer consisting essentially of $SiO_2$ units, $(CH_3)_3SiO_{0.5}$ units, Vinyl $(CH_3)_2SiO_{0.5}$ units; and
  c. a cross-linking Si-H component, consisting essentially of $(CH_3)_3SiO_{0.5}$ units, $(CH_3)_2SiO$ units and $CH_3HSiO$ units.

2. A pharmaceutical composition according to claim 1, further comprising a catalytic amount of a platinum metal-based catalyst dissolved therein.

3. A pharmaceutical composition according to claim 1, wherein component a) comprises 20–100 parts by weight of vinyl terminated linear organopolysiloxane having a viscosity of 500–200,000 centistokes (at 25° C.) of the general formula:

$$R''_a H_b SiO_{\frac{4-a-b}{2}}$$

wherein $R_2$ is lower alkyl and $n$ is an integer of about 200–1600;

b. comprises 0–50 parts by weight of an organopolysiloxane copolymer consisting essentially of:
  i. $R'_3SiO_{0.5}$ units
  ii. $R'_2ViSiO_{0.5}$ units, and
  iii. $SiO_2$ units
  wherein Vi is a vinyl group, $R'_2$ and $R'_3$ are each a saturated, lower alkyl, at least 50% of R' being methyl; and c. comprises 5–15 parts by weight of an organohydrogen polysiloxane of the general formula

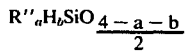

wherein R'' is lower alkyl, $a$ and $b$ are each positive numbers, the ratio of $a:b$ is 0.5–10; the sum of $a+b$ is 1–2.5; at least three hydrogen atoms linked to different Si atoms are present per molecule; and said component contains 50–500 molar percent, based on unsaturated end groups contained in components (a) and (b), of vinyl groups attached to Si–H.

4. A pharmaceutical composition according to claim 3 adapted for implantation into a human or animal body.

5. A pharmaceutical composition according to claim 3 in the form of a prosthetic device.

6. A pharmaceutical composition according to claim 3 wherein said medicament is a steroid.

7. A pharmaceutical composition according to claim 3 in a form suitable for intrauterine or intravaginal administration.

8. A pharmaceutical composition according to claim 7 in the form of a vaginal ring.

9. A pharmaceutical composition according to claim 8, wherein said medicament is a steroid.

* * * * *

UNITED STATES PATENT AND TRADEMARK OFFICE
CERTIFICATE OF CORRECTION

PATENT NO. : 4,012,497
DATED : MARCH 15, 1977
INVENTOR(S) Gisela Schopflin

It is certified that error appears in the above-identified patent and that said Letters Patent are hereby corrected as shown below:

In Claim 3, column 15, line 10, the formula should read as follows:

-- 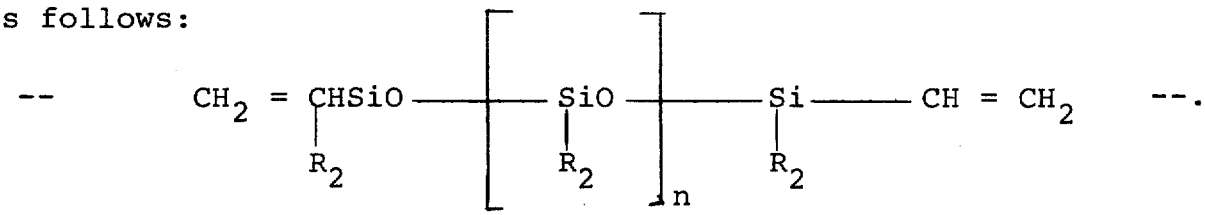 --.

In Claim 3, column 16, lines 1-6, the formula should read as follows:

-- 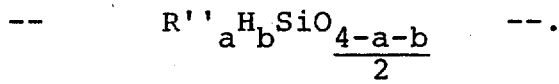 --.

Signed and Sealed this

Tenth Day of May 1977

[SEAL]

Attest:

RUTH C. MASON
Attesting Officer

C. MARSHALL DANN
Commissioner of Patents and Trademarks

UNITED STATES PATENT AND TRADEMARK OFFICE
CERTIFICATE OF CORRECTION

PATENT NO. : 4,012,497

DATED : March 15, 1977

INVENTOR(S) : GISELA SCHOPFLIN

It is certified that error appears in the above-identified patent and that said Letters Patent are hereby corrected as shown below:

Claim 3, column 15, line 10: the formula should read as follows:

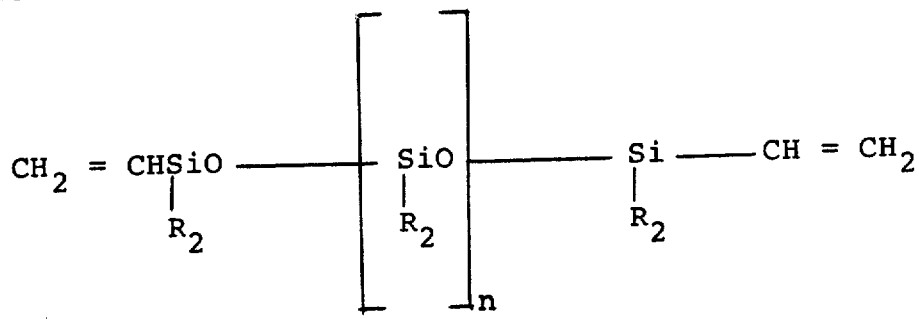

Claim 3, column 16, lines 1-6, the formula should read

-- 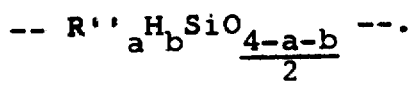 --.

This certificate supersedes certificate issued May 10, 1977.

Signed and Sealed this

Thirteenth Day of June 1978

[SEAL]

Attest:

RUTH C. MASON
Attesting Officer

DONALD W. BANNER
Commissioner of Patents and Trademarks